(12) United States Patent
Wright

(10) Patent No.: US 6,517,524 B2
(45) Date of Patent: Feb. 11, 2003

(54) OCCLUSIVE CANNULA FOR AORTIC BLOOD FLOW AND AIR VENTING

(75) Inventor: John T. M. Wright, Denver, CO (US)

(73) Assignee: Genesse Biomedical, Inc., Denver, CO (US)

(*) Notice: Subject to any disclaimer, the term of this patent is extended or adjusted under 35 U.S.C. 154(b) by 0 days.

(21) Appl. No.: 09/784,577

(22) Filed: Feb. 15, 2001

(65) Prior Publication Data
US 2002/0111583 A1 Aug. 15, 2002

(51) Int. Cl.[7] .............................................. A61M 29/00
(52) U.S. Cl. ...................... 604/284; 604/509; 604/96.01
(58) Field of Search ............................. 604/284, 96.01, 604/912, 915, 920, 921, 500, 508–510

(56) References Cited

U.S. PATENT DOCUMENTS

| | | | |
|---|---|---|---|
| RE35,352 E | 10/1996 | Peters | 604/96.01 |
| 5,833,671 A | 11/1998 | Macoviak et al. | 604/247 |
| 6,048,331 A | 4/2000 | Tsugita et al. | 604/96.01 |
| 6,059,757 A | 5/2000 | Macoviak et al. | 604/247 |
| 6,068,608 A | 5/2000 | Davis et al. | 604/96.01 |
| 6,132,397 A | 10/2000 | Davis et al. | 604/101 |
| 6,176,851 B1 | 1/2001 | Tsugita et al. | 604/96.01 |

OTHER PUBLICATIONS

Milsom, FP & Mitchell, SJ, Ann. Thorac. Surg. 66: 785–91 (1998).

*Primary Examiner*—Patrick Brinson
(74) *Attorney, Agent, or Firm*—Swanson & Bratschun LLC

(57) ABSTRACT

A unitary, integral dual lumen occlusive cannula having two lumina of a size, e.g. 0.05 to 0.15 cm$^2$, sufficient for bypass blood flow, having an inlet formed in a configuration for complete removal of residual air and debris from the circulatory system is disclosed.

8 Claims, 1 Drawing Sheet

OCCLUSIVE CANNULA FOR AORTIC BLOOD FLOW AND AIR VENTING

This invention relates to aortic cannula used in heart valve surgery.

More specifically, this invention relates to devices and methods for complete removal of residual air and debris from the circulatory system following cardiopulmonary bypass heart surgery before restoring normal blood circulation through the heart.

BACKGROUND OF THE INVENTION

The use of cardiopulmonary bypass in heart valve surgery is a well-established method for maintaining blood circulation during open heart surgery. Cardiopulmonary bypass is accomplished by inserting one or more cannula into the vena cava, and drawing venous blood into the heart-lung machine. Oxygenated blood from the heart-lung machine is then returned to the patient's aorta via an aortic cannula placed in the ascending aorta. The aorta is then cross-clamped immediately below the insertion site of the aortic cannula, thus isolating the aortic arch from the aortic valve. Prior to opening the ascending aorta or atrium a cold cardioplegia solution is pumped into the aorta by means of a small cannula placed in the ascending aorta below the aortic cross clamp. This is called antegrade cardioplegia delivery and results in arrest of the heart. This is often followed by a second delivery of cardioplegia solution delivered by a cannula inserted into the coronary sinus, the venous drainage vessel of the coronary. The retrograde delivery of cardioplegia flows first through the coronary veins, the myocardium and the passes into the coronary arteries hence through the coronary sinuses into the aorta. The solution exits the aorta via the retrograde cardioplegia catheter. Cardioplegia delivery often in 500 cc boluses is delivered approximately every 20 to 30 minutes to the arrested heart. Once cardiopulmonary bypass has been established and the heart arrested the aorta may be opened if the surgery is to be performed on the aortic valve, or the left atrium if surgery is to be performed on the mitral valve. Following the completion of valve surgery, the aorta or atria are closed, and the task of removing air in the atrium, ventricle and aorta falls to the surgeon. Milsom P F, and Mitchell S. J. *A dual-vent left heart deairing technique markedly reduces carotid artery microemboli.* Ann Thorac Surg. September 1998;66(3):785–91, describe a method for reducing microemboli. A further source of microemboli not discussed by Milson may be shed from the site of the aortic cross clamp, in patients with arterioscerotic plaque in the aorta.

This invention provides for the aortic venting method described by Milsom, obviates and aortic cross clamp by using an occlusive balloon in the ascending aorta.

Cannula and occluder devices for redirecting the blood are, of course, known. For example, Macoviak, et. al. U.S. Pat. Nos. 5,833,671, 5,827,231 and 6,059,757 disclose various catheters with retrograde and antegrade fluid flow. U.S. Pat. Nos. 6,048,331 and 6,176,851 to Tsugita and Maahs disclose a device for occluding a vessel and performing other functions which provides cannula for selectively introducing cardioplegia solution or for withdrawing blood, emboli, etc. from one side of the occluder. Tsugita and Maahs suggest a "one stick" device but the device suggested is a combination of two devices through the same incision in the aorta. Davis, et. al. U.S. Pat. Nos. 6,068,608 and 6,132,397 disclose an aortic arch infusion clamp which has plural lumina but does not contemplate and is not useful for removing air or debris from the surgical site following open heart surgery.

It is an object of this invention to provide a multi-luminal device to permit bypass flow to continue and, for a period at the same time, to expel blood, along with air or particle emboli, using the beating heart as the pump.

SUMMARY OF THE INVENTION

The present invention is a device and method for redirecting arterial blood flow on one side of an occluder and simultaneously removing blood containing air emboli on the other side of the occluder through a passage approximately the same cross-sectional flow area as the arterial delivery area, thus providing in one simple device means for isolating the proximal and distal ascending aorta.

The invention is embodied in a unitary device comprising an L curved cannulated body having proximal and distal ends that includes two approximately flow cross-sectional lumina of a size large enough to maintain bypass circulation, a balloon occluder secured around the distal, shorter, end of the cannulated body, the first lumen opening at the distal end of the cannulated body such that, in use, the first lumen is in fluid communication with the vessel on a first side distal of the occluder to maintain bypass circulation in the vessel a second lumen having an opening that, in use, is in fluid communication with a second side proximal of the occluder and a fluid conduct for inflating the balloon occluder to form a seal with the vessel in which, in use, the occluder resides for preventing fluid flow in the vessel from one side of the occluder to the other side of the occluder.

The invention is also embodied in an improvement in methods of performing cardiopulmonary bypass heart surgery in which the flow of blood of a patient from the venous system is bypassed to an oxygenator and the needed surgery is done to the valves or other structures of the heart. In this sense, this is an improvement over the methods described by Milsom et. al. and in the very extensive literature on open heart surgery. The improvement comprises inserting into the ascending aorta of the patient a cannulated body having a proximal end and a distal end and being curved adjacent the distal end, said cannulated body being constructed and configured to define a first curved lumen having a proximal end and a distal end and a second lumen having a proximal end and a distal inlet formed in the cannulated body such that when in use, the inlet is proximate the termination of flow in the aorta of blood from the heart and means for causing the occluder to expand or to contract. The surgical procedure is performed, the flow of blood from the venous system into the heart is restored and the heart is restarted, pumping blood into the ascending aorta. Blood pumped by the heart is removed from the aorta through the inlet in the cannulated body to remove air or other emboli. Once the air or other emboli are removed, the cannulated body is removed from the ascending aorta and the incision closed.

Briefly, as a device, the invention is a cannulated body having a proximal end for, in use, residing outside a blood vessel and a distal end for, in use, residing inside a blood vessel, the cannulated body being curved adjacent the distal end, an expandable occluder secured around the cannulated body proximate the distal end thereof, the cannulated body being constructed and configured to define a first curved lumen having a proximal end and a distal end, and a second lumen having a proximal end and a distal inlet formed in the cannulated body adjacent the proximal side of the occluder.

DESCRIPTION OF THE PREFERRED EMBODIMENT

The following description is of the presently preferred embodiment of the invention which exemplifies the inventive concept of the invention but does not limit the scope of the claims.

The invention is preferably assembled from its constituent components into a unitary device comprising an L curved cannulated body having a proximal end and a distal end, the L curve being closer to the distal end of the cannulated body, an occluder balloon secured around the distal, shorter, end of the cannulated body, the cannulated body defining first and second lumen generally of about the same cross-sectional flow area and each being large enough to maintain at least minimal bypass blood flow during surgery, the first lumen opening, in use, such that it is in fluid communication with the vessel on a first side, e.g. the distal side, the second lumen opening such that, in use, it is in fluid communication with the vessel in which it is inserted on a second side, e.g. the proximal side, of the ocduder and a fluid conduct for inflating the balloon occluder to form a seal with the vessel for preventing fluid flow in the vessel from one side of the occluder to the other side of the occluder.

The device of this invention is preferably configured and constructed such that it can be passed through an aperture in the anterior side of the ascending aorta and reside in the aorta to introduce bypassed blood flow into the aorta distal of the occluder and to remove blood from the re-started beating heart to remove all air bubbles and debris before restoring circulation from the beating heart. Surgeons may find other uses for the device also; however, the discussion that follows should be considered in the context of the use just mentioned.

Figure 1:
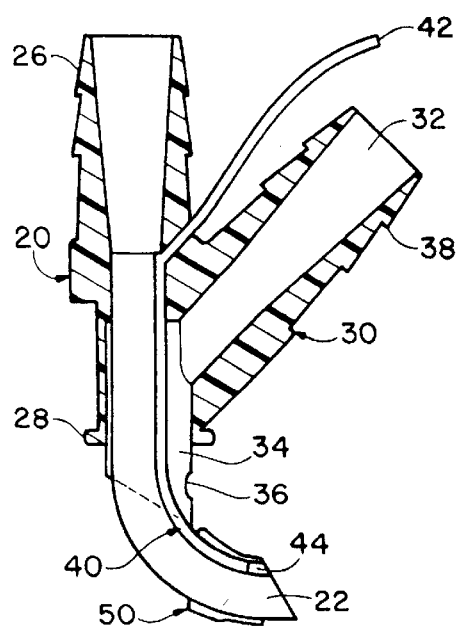
FIG. 1 depicts the device of this invention in side elevational cross-section.
Figure 2:
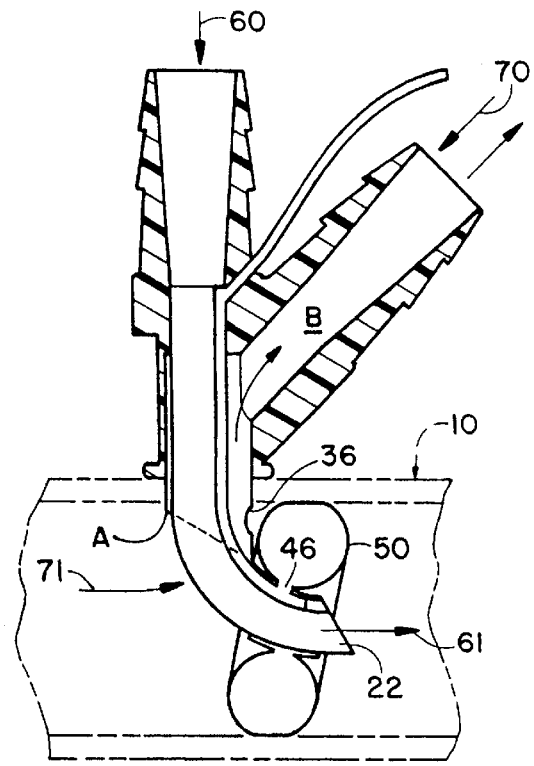
FIG. 2 depicts the device of this invention in side elevational cross-section shown as it would be used, occluding an artery with fluid flow in opposite directions on the respective sides of the occluder. When used as intended in the ascending aorta, the direction of blood flow from the beating heart would be from left to right in the Figure as drawn.
Figure 3:
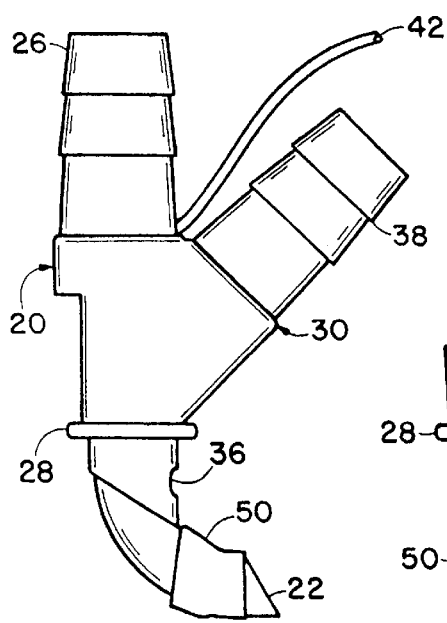
FIG. 3 depicts the device of this invention in side elevational view with the occluder balloon deflated.

Referring to the drawings, FIGS. 1, 2, 3 and 4, in particular, the device of this invention comprises an L curved cannulated body 20 having proximal and distal ends, the cannulated body defining a curved first lumen, into which fluid may be introduced, as shown at 60 and discharged at its outlet as shown at 61, shown in FIG. 2, as the arrows indicate. The direction of blood flow depends, of course, on how the device is used and where it is placed. The first lumen defines a distal end, normally the exit end, 22 a proximal end, normally the input end, 24. The cannulated body is curved to define an L shape the curve, in the preferred embodiment, be closer to the distal end of the conduit than to the proximal end of the conduit. The first lumen is normally used and is sufficiently large enough to maintain bypass blood during surgery. Thus, the cross-sectional area of the first lumen would normally be about 0.05 to 0.2 cm² or larger.

The L curved cannulated body also defines means, such as a series of annular protrustions, 26 adjacent the inlet 24 on the external surface of the cannulated body for securing a flexible tube to the device. It also comprises, in the preferred embodiment, a flange 28 on the external surface of the cannulated body about the center of the cannulated body for forming a seal with the vessel into which its inserted when in use.

Figure 5:
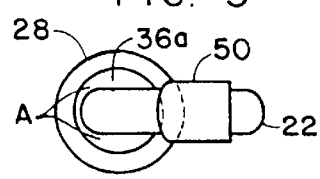
FIG. 5 is a bottom view, as the device is depicted in the drawings, of the device of this invention.

The L curved cannulated body also defines a second lumen of about the same cross-sectional flow area, generally in the range of about 0.05 to 0.2 cm² cross sectional flow having a proximal opening 32, normally an outlet for removing emboli-carrying blood, and an inlets 36 and 36a for blood being pumped by the heart into the aorta immediately upon restarting the heart after surgery. The inlet 36a is positioned at the end of the blood flow path in the aorta adjacent the occluder. This the region to which air bubbles will accummulate and from which air bubbles are most efficiently removed from the circulatory system. The opening 36a, best shown in FIGS. 2 and 5, is a generally annular space around the first lumen. The combined flow cross-sectional area of the inlets 36 and 36a, the annular flow path of the lumen 32, is approximately equal to the flow area of the first lumen. The blood flow path is indicated by the arrows A, into the annular area 36a formed between the cuff at the bottom of the structure forming the second lumen and the arrow B indicating flow into the inlet 36. The inlets and second lumen must have sufficient flow capacity to permit removal from the circulatory system of the patient all or at least a very substantial portion of the output of the beating heart and, thus, is generally about the same cross-sectional flow size as the first lumen or only slightly smaller. The inlet 36 is formed in the cannulated body between the flange 28 and the occluder such that air bubbles being carried by the blood in the ascending aorta will be carried to the inlet 36 and out of the circulatory system before the bypass circulation is removed. When all, or substantially all, of the air and debris has been removed and the heart is pumping clean blood, it is a simple task to remove the device from the aorta and return the circulatory blood flow path through the heart. No other known device provides this advantage. Flow arrow 70 and 71 suggest the obvious, that flow may be in either direction as determined by the surgeon to meet particular needs other than that described. As will be seen in FIGS. 1 and 2 a portion of the lumen may be a chamber 34 around a portion of the curved first lumen. This is a convenient, preferred structural feature but is not essential to the invention.

An inflation fluid conduit 40 extends from outside the cannulated body through the wall of the curved cannulated body into the first lumen from a proximal end 42 to a plug 44 in the distal end and is secured in fluid communication through a passage 46 through the wall of the cannulated body with a balloon occluder 50 which is positioned around the curved first conduit proximate the distal end thereof. Any convenient form of inflation flow conduit may be used, including one that does not enter either of the lumen.

Figure 6:
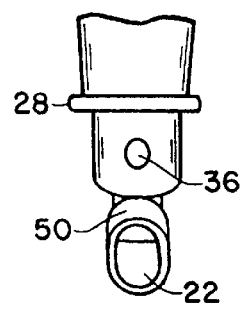
FIG. 6 depicts a portion of the bottom right side, as the device is depicted in FIG. 3 of the drawings.
Figure 4:
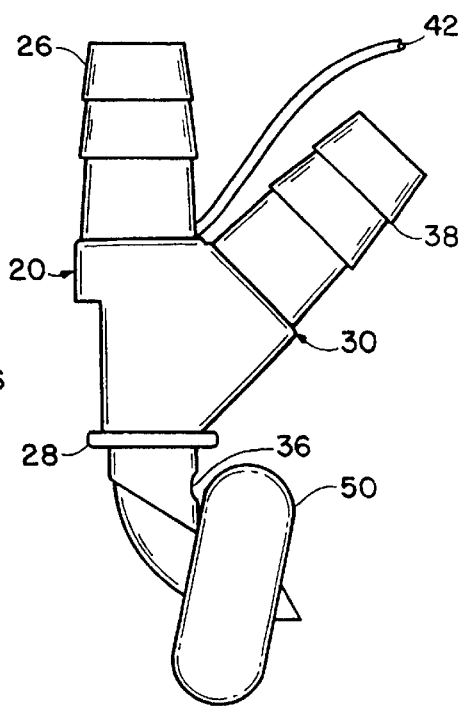
FIG. 4 depicts the device of this invention in side elevational view with the occluder balloon inflated.

The position of the occluder proximate the distal end of the curved first conduit is depicted specifically in FIGS. 5 and 6. Fluid, air typically, flowing in at proximal end 42 of the conduit 40 inflates the occluder, as shown in FIGS. 2 and 4, to close the vessel 10 to occlude the vessel which, in use, it resides.

Unlike the prior art devices, the present invention provides two lumen of a size sufficient to circulate bypass blood and to remove air bubbles and particulate matter. The closest known prior art devices could, in some instances, be used for one or the other of these functions, but not both. The ability to provide both functions in one simple device is of great consequence in reducing the time and trauma of open heart surgery and the safety of re-starting the heart circulation.

Referring again to FIG. 2, it is pointed out that when the device of this invention is positioned in the ascending aorta according to the method of the invention, the blood flow from the heart is from left to right, in the direction of the arrow 61, although at this stage in the procedure no blood from the heart passes the occluder. As the heart is re-started the flow of blood carrying residual air and debris is from the left, as shown in FIG. 2, to the inlet 36 which is at the termination of the flow path in the aorta. The air bubbles and debris carried by the blood will be carried into the inlet 36 and removed from the circulatory system. Herein lies the most important benefit of the present invention.

The invention is, thus, embodied as a very space efficient simple and inexpensive device for both arterial blood flow, blood containing air fluid removal to prevent cerebral microemboli and atraumatic isolation of the ascending aorta, also to minimize micro emboli due to plaque disruption due to aortic cross-clamping. The device providing a major simplification over the devices of the known prior art.

The device is typically made of a combination of thin wall stainless steel or extrudable synthetic polymer, polysulfone or ABS or polycarbonate for example, the balloon occluder being made typically of a flexible synthetic polymer, silicone rubber or latex rubber, the entire assembly being bonded together into a unitary structure by heat sealing or thermal welding or with adhesive into a unitary disposable product than can be sterilized by the supplier and used in the operating room without sterilization and with consider savings of precious surgical time. The materials and methods of fabrication of unitary devices composed of polymeric materials by thermal welding and adhesive bonding are well known.

The invention is also embodied in a method for performing open heart surgery comprising, inter alia, passing through an incision in a blood vessel, e.g. the ascending aorta, a unitary device comprising an L curved cannulated body having proximal and distal ends that includes two approximately equal diameter lumina of a size large enough to maintain bypass circulation, a balloon occluder secured around the distal shorter, end of the cannulated body, the first lumen opening at the distal end of the cannulated body such that, in use, the first lumen is in fluid communication with the vessel on a first side distal of the occluder to maintain bypass circulation in the vessel, a second lumen having an opening that, in use, is in fluid communication with a second side proximal of the occluder and a fluid conduct for inflating the balloon occluder to form a seal with the vessel in which, in use, the occluder resides for preventing fluid flow in the vessel from one side of the occluder to the other side of the occluder.

The device may preferably comprise a cannulated body having a proximal end and a distal end and being curved adjacent the distal end, said cannulated body being constructed and configured to define a first curved lumen having a proximal end and a distal end defining a first flow path through the distal end, and a second flow path having a proximal end and a distal end, an expandable occluder around the cannulated body adjacent the distal end thereof, and a lumen in fluid communication with the occluder for causing the occluder to expand or to contract the cannulated body being so configured and constructed that, in use, the first flow path is in fluid communication with the interior of the vessel on one side of the occluder and the second passageway is in fluid communication with the vessel on the other side of the occluder such that when the occluder is expanded it closes the vessel to flow from one side to the other side permitting, independently, introduction of or withdrawal of fluid from the vessel on the respective sides of the occluder.

Industrial Application

The device and method is useful in surgery and in the medical instrument field.

What is claimed is:

1. An integral dual lumen, dual flow cardiovascular occluder device suitable for use in cardiopulmonary bypass surgery for removing all or substantially all residual air and debris from the circulatory system following cardiopulmonary bypass heart surgery before restoring normal blood circulation through the heart and vascular system, said device being constructed and configured to be inserted through the wall of a blood vessel to occlude the vessel and to permit simultaneous introduction to or removal of different liquids into or from the vessel on the respective sides of the occluder, the occluder comprising:

a) a curved cannulated body defining:
  i) a first lumen having a proximal end and a distal end, the first lumen forming a first curved liquid flow path of about 0.05 to 0.2 $cm^2$ cross sectional flow diameter sufficient for bypass blood flow; and
  ii) a second lumen defining a second flow path of about 0.05 to 0.2 $cm^2$ cross sectional flow diameter, said second flow path having a proximal opening and distal inlet formed in the cannulated body, said inlet being configured and disposed such that when the device is in use the inlet is proximate the termination of blood flow in the vessel such that blood in the vessel carrying air bubbles can be removed from the vessel;
 b) an annular balloon occluder disposed around a portion of the curved cannulated body defining the first curved lumen proximate the distal end of the cannulated body; and
 c) means for expanding the annular balloon occluder in a blood vessel when the device is in use.

2. The device of claim 1 wherein a portion of the second lumen is a chamber partially surrounding the curved first lumen.

3. A unitary, integral dual lumen, dual flow cardiovascular occluder device constructed and configured to be inserted through the wall of a blood vessel to occlude the vessel and to permit simultaneous introduction to or removal of different liquids into or from the vessel on the respective sides of the occluder, the occluder comprising:

a) a cannulated body having a proximal end for, in use, residing outside a blood vessel and a distal end for, in use, residing inside a blood vessel, said cannulated body being curved adjacent the distal end, said cannulated body being constructed and configured to define a first curved lumen having a proximal end and a distal end, and a second lumen having a proximal end and a distal inlet formed in the cannulated body such that, when in use, the inlet is proximate the termination of flow of blood in the vessel, said distal inlet having a cross sectional flow diameter sufficient for bypass blood flow;
 b) an expandable occluder secured around the cannulated body proximate the distal end thereof; and
 c) means for causing the occluder to expand or to contract.

4. A method of performing cardiopulmonary bypass heart surgery comprising the steps of:

a) redirecting the blood flow from the venous system of the patient from the heart to an oxygenator;
b) inserting into the ascending aorta of the patient a cannulated occluder comprising:
   i) a cannulated body having a proximal end and a distal end and being curved adjacent the distal end, said cannulated body being constructed and configured to define a first curved lumen having a proximal end and a distal end, and a second lumen having a proximal end and a distal inlet formed in the cannulated body such that when in use, the inlet is proximate the termination of flow of blood from the heart;
   ii) an expandable occluder secured around the cannulated body proximate the distal end thereof; and
   iii) means for causing the occluder to expand or to contract;
c) expanding said occluder;
d) performing the surgery;
e) opening the flow of blood from the venous system into the heart and restarting the heart;
f) removing blood pumped by the heart from the aorta through the inlet in the cannulated body to remove air or other emboli; and
g) removing the cannulated body from the ascending aorta.

5. A dual lumen, dual flow occluder device suitable for use in surgery, comprising:
   a) an L curved cannulated body constructed and configured to define:
      i) a first lumen having a proximal end configured and constructed for residing outside a blood vessel and a distal end configured and constructed for residing inside a blood vessel, said first lumen having openings therein in fluid communication with each other, the first lumen forming a first curved liquid flow path; and
      ii) a second lumen having a proximal opening and a distal opening in fluid communication with each other, the distal opening being formed in the cannulated body;
   b) an annular occluder disposed around a portion of the curved cannulated body proximate the distal end of the cannulated body; and
   c) means for expanding the occluder inside a blood vessel; wherein the distal opening of the second lumen is adjacent the proximal side of the occluder and has a cross sectional diameter sufficient for bypass blood flow.

6. An occlusive cannula comprising:
   a) a cannulated body comprising a proximal end for, in use, residing outside a blood vessel and a distal end for, in use, residing inside a blood vessel, and being curved adjacent the distal end;
   b) an expandable occluder secured around the cannulated body proximate the distal end thereof, said cannulated body being constructed and configured to define:
      i) a first curved lumen having a proximal end with a blood flow opening therein and a distal end with a blood flow opening therein, the blood flow openings being in fluid communication with each other through the first lumen; and
      ii) a second lumen having a proximal end and a distal inlet formed in the cannulated body adjacent the proximal side of the occluder, said distal inlet having a cross sectional diameter sufficient for bypass blood flow.

7. The occlusive cannula of claim 6 wherein said cannulated body defines the distal inlet in the second lumen such that said distal inlet in said second lumen comprises a generally annular space around the first lumen.

8. The occlusive cannula of claim 7 wherein said cannulated body defines the distal inlet in the second lumen such that said distal inlet also comprises a passage through the wall of the first lumen adjacent to said occluder.

* * * * *